US005738790A

United States Patent [19]

Hagen et al.

[11] Patent Number: 5,738,790
[45] Date of Patent: *Apr. 14, 1998

[54] COMPOSITE MEMBRANES FOR SOLID PHASE EXTRACTIONS AND REACTIONS

[75] Inventors: Donald F. Hagen, Woodbury; Paul E. Hansen, Lake Elmo; Craig G. Markell, White Bear, all of Minn.

[73] Assignee: Minnesota Mining and Manufacturing Company, St. Paul, Minn.

[*] Notice: The term of this patent shall not extend beyond the expiration date of Pat. No. 5,639,372.

[21] Appl. No.: 812,365

[22] Filed: Mar. 5, 1997

Related U.S. Application Data

[60] Continuation of Ser. No. 627,324, Apr. 1, 1996, Pat. No. 5,635,060, which is a division of Ser. No. 449,518, May 23, 1995, Pat. No. 5,529,686, which is a continuation of Ser. No. 276,167, Jul. 15, 1994, abandoned.

[51] Int. Cl.$^6$ ..................................................... B01D 15/08
[52] U.S. Cl. ............................. 210/635; 210/656; 210/658
[58] Field of Search ................................. 210/635, 656, 210/658, 198.2, 198.3, 502.1, 505

[56] References Cited

U.S. PATENT DOCUMENTS

| | | | |
|---|---|---|---|
| 4,153,661 | 5/1979 | Ree et al. | 264/120 |
| 4,344,775 | 8/1982 | Klein | 55/75 |
| 4,648,977 | 3/1987 | Garg et al. | 210/673 |
| 4,650,575 | 3/1987 | White | 210/183 |
| 4,664,812 | 5/1987 | Klein | 210/679 |
| 4,740,219 | 4/1988 | Kulprathipanja et al. | 55/16 |
| 4,744,374 | 5/1988 | Deffeves | 131/331 |
| 4,810,381 | 3/1989 | Hagen et al. | 210/502.1 |
| 4,826,497 | 5/1989 | Marcus et al. | 604/359 |
| 4,828,698 | 5/1989 | Jewell | 210/266 |
| 4,855,154 | 8/1989 | Gioffre et al. | 426/417 |
| 4,906,378 | 3/1990 | Hagen et al. | 210/635 |
| 4,933,229 | 6/1990 | Insley | 428/224 |
| 4,971,736 | 11/1990 | Hagen et al. | 264/22 |
| 5,013,335 | 5/1991 | Marcus | 55/70 |
| 5,071,565 | 12/1991 | Fritz et al. | 210/692 |
| 5,071,610 | 12/1991 | Hagen et al. | 264/120 |
| 5,100,596 | 3/1992 | Haag et al. | 264/42 |
| 5,108,597 | 4/1992 | Funkenbusch | 210/198.2 |
| 5,147,539 | 9/1992 | Hagen et al. | 210/198.3 |
| 5,207,915 | 5/1993 | Hagen et al. | 210/635 |
| 5,279,742 | 1/1994 | Markell et al. | 210/638 |
| 5,328,758 | 7/1994 | Markell et al. | 428/281 |
| 5,417,678 | 5/1995 | Baumann et al. | 604/333 |
| 5,468,536 | 11/1995 | Whitcomb et al. | 428/98 |
| 5,529,686 | 6/1996 | Hagen et al. | 210/198.2 |
| 5,639,372 | 6/1997 | Hagen | 210/638 |

FOREIGN PATENT DOCUMENTS

| | | | |
|---|---|---|---|
| 0284227 | 9/1988 | European Pat. Off. | 210/198.2 |

OTHER PUBLICATIONS

Chriswell & D.T. Gjerde, *Anal. Chem.*, 1982, 54, 1911–1913.

Chriswell et al., Use of Silicalite Molecular Sieve for Gas Chromatographic Determination of Permanent Gases and Volatile Hydrocarbons Emitted During Coal Processing, *J. Chromatogr.*, 1987, 405, 213–221.

Colella et al., "Lead Removal from Waste Waters Using Chabizite Tuff", Perspectives in Molecular Sieve Science, Flank, W.H. and Whyte Jr., T.E., Eds. *ACS Symposium Series*, 386, Am. Chem. Soc., Washington, DC 1988 pp. 500–510.

Errede, et al., "Chemical Modified Surfaces in Science and Industry", Gordon and Breach Science Publishers, New York, 1998, 91–104.

Flanigen et al., "Silicalite, a New Hydrophobic Crystalline Silica Molecular Sieve", *Nature*, 1978, 271, 512–516.

Hagen et al., "Membrane Approach to Solid Phase Extraction", *Anal. Chim. Acta*, 1990, 236, 157–164.

Markell et al., "New Technologies in Solid Phase Extraction," *LC/GC* 1991 9, No. 5, pp. 332–337.

Otto et al., "Adsorption of Hydrocarbons and Other Exhaust Components on Silicalite", *Ind. Eng. Chem. Res.*, 1991, 30, 2333–2340.

Rostad, et al., "Bonded–Phase Extraction Column Isolation of Organic Compounds in Groundwater at a Hazardous Waste Site", *Anal. Chem.*, 1984, 56, 2856–2860.

Schultz–Sibbel et al., Analytical Investigation of the Properties and uses of a New Hydrophobic Molecular Sieve, *Talanta*, 1982, 29, 447–452.

Database WPI Week 9213, Derwent Publications Ltd., London, GB; AN 92–101976 & JP,A,04045829 (abstract) (14 Feb. 1992).

Patent Abstracts of Japan, vol. 18, No. 371 (C–1224) & JP, A,06 099044 (Agency of Ind. Science & Technol.) (abstract) 12 Apr. 1994).

*Primary Examiner*—Ernest G. Therkorn
*Attorney, Agent, or Firm*—Lorraine R. Sherman

[57] ABSTRACT

A solid phase extraction or chromatographic medium comprises a porous nonwoven fibrous matrix comprising at least one of polytetrafluoroethylene and blown microfibers, and sorptive or reactive hydrophobic siliceous molecular sieve particulates enmeshed in said matrix, the ratio of molecular sieves to matrix being in the range of 40:1 to 1:40.

22 Claims, No Drawings

COMPOSITE MEMBRANES FOR SOLID PHASE EXTRACTIONS AND REACTIONS

This is a continuation of application Ser. No. 08/627,324 filed Apr. 1, 1996, now U.S. Pat. No. 5,635,060 which was a division of application Ser. No. 08/449,518 filed May 23, 1995, now U.S. Pat. No. 5,529,685 which was a continuation of application Ser. No. 08/276,167, filed Jul. 15, 1994, now abandoned.

TECHNICAL FIELD

This invention relates to articles which are composite structures and a method therefor, the articles comprising a polytetrafluoroethylene (PTFE) or melt blown (BMF) nonwoven matrix having enmeshed therein molecular sieves. The articles are useful as selective sorptive or reactive media for applications in separations, purifications, diagnostics, environmental extractions, clinical extractions, catalysis, and the like.

BACKGROUND OF THE INVENTION

Separation science and purification technologies are well known in the art and have received increased attention in recent years because of environmental concerns and need for environmental clean-up. A technique in this art is solid phase extraction (SPE), which has received considerable attention recently. SPE is widely used for pre-concentration and cleanup of analytical samples, for purification of various chemicals, and for large scale applications such as removal of toxic or valuable substances from many, predominantly aqueous solutions as is disclosed in U.S. Pat. No. 5,071,565. Others such as Rostad et al., "Bonded-Phase Extraction Column Isolation of Organic Compounds in Groundwater at a Hazardous Waste Site", *Anal. Chem.* 1984, 56, 2856–2860, have utilized particle packed columns for SPE. SPE-utilizing particle loaded membranes has been taught by Hagen et al., "Membrane Approach to Solid Phase Extraction," *Anal. Chim. Acta* 1990, 236, 157–164 and Markell et al., "New Technologies in Solid Phase Extraction," *LC/GC* 1991, 9, Number 5, U.S. Pat. Nos. 4,810,381, 4,906,378, 4,971,736, 5,071,610, 5,147,539, 5,207,915, and 5,279,742.

Use of molecular sieves in separation science is also well known and has been described in the chemical literature. For example, "Lead Removal from Waste Waters Using Chabazite Tuff" was reported by C. Colella and M. Pansini in "Perspectives in Molecular Sieve Science"; Flank, W. H., and Whyte Jr., T. E., Ed.; *ACS Symposium Series* 368; American Chemical Society: Washington, D.C., 1988, chapter 32. K. Otto et al. used a zeolite in "Adsorption of Hydrocarbons and Other Exhaust Components on Silicalite" in *Ind. Eng. Chem. Res.* 1991 30, 2333–2340, and C. D. Chriswell et al. described "Use of Silicalite Molecular Sieve for Gas Chromatographic Determination of Permanent Gases and Volatile Hydrocarbons Emitted During Coal Processing" in the *J. Chromatogr.* 1987, 405, 213–220. C. D. Chriswell and D. T. Gjerde sampled stack gas for sulfur dioxide with a molecular sieve adsorbent as reported in *Anal. Chem.* 1982, 54, 1911–1913. G. M. W. Schultz-Sibbel et al. in "Analytical Investigation of the Properties and Uses of a New Hydrophobic Molecular Sieve" (*Talanta*, 1982, 29, 447–452) characterized distribution coefficients and capacities of silicalite. Unlike aluminosilicate zeolites, which are hydrophilic, silicalite is hydrophobic/organophilic and selectively adsorbs organic molecules over water as reported by E. M. Flanigen et al., "Silicalite, a New Hydrophobic Crystalline Silica Molecular Sieve" in *Nature* 1978, 271, 512–516.

Use of molecular sieves in separation science has also been described in the patent literature. For example, U.S. Pat. No. 5,100,596 provides a method for synthesis of a membrane comprised purely of a molecular sieve useful in the separation of gaseous or liquid mixtures. The patent further states (col. 1, lines 26–28) that "The potential of zeolites as components in microporous membranes has not been fully explored." U.S. Pat. No. 5,013,335 teaches a process for sequestering ammonia and the odor associated therewith using a crystalline siliceous molecular sieve. U.S. Pat. No. 4,826,497 describes fibrous absorbent articles such as diapers and bandages and the like which contain molecular sieves for deodorizing. U.S. Pat. No. 4,855,154 claims a process for deodorizing marine oils using molecular sieves and U.S. Pat. No. 4,648,977 provides a process for removing toxic organic materials from aqueous solutions in contact with organophilic molecular sieves. European Patent Application 88301879.8 teaches a process for the recovery of halogenated hydrocarbons in a gas stream. The stream is passed through a bed of hydrophobic molecular sieves which sorbs the hydrocarbons.

Membranes comprising sorptive media in a polytetrafluoroethylene (PTFE) fibril matrix useful in separation science has been described in U.S. Pat. No. 5,071,610. A method for isolating organic materials using SPE comprises a polytetrafluoroethylene (PTFE) fibril matrix in which are enmeshed sorptive particles and a novel article and also stacked article for use as an extraction medium is disclosed in U.S. Pat. No. 5,279,742. U.S. Pat. No. 5,328,758 discloses particle loaded melt blown microfiber (BMF) composites for SPE.

SUMMARY OF THE INVENTION

Briefly, the present invention provides a solid phase extraction or chromatographic medium comprising (a) a porous nonwoven fibrous matrix preferably comprising polytetrafluoroethylene (PTFE) fibrils or blown microfibers (BMF), and (b) sorptive or reactive hydrophobic siliceous molecular sieve particulates enmeshed in said matrix, the ratio of molecular sieves to matrix being in the range of 40:1 to 1:40, preferably 19:1 to 1:4.

Preferably, the enmeshed particulates comprise (1) at least 30 and up to 100 weight percent, preferably 35 to 100 weight percent, of hydrophobic siliceous molecular sieves entrapped in the matrix, and (2) 70 to 0 weight percent, preferably 65 to 0 weight percent, of preferably porous, organic-coated or uncoated particulates different from said hydrophobic molecular sieves.

In another aspect, a method of concentrating by sorption or reaction of at least one organic component from a fluid comprises the step of passing a fluid (i.e., a liquid or gas) containing at least one organic component through or by at least one solid phase extraction medium comprising (a) a matrix comprising polytetrafluoroethylene (PTFE) fibrils or blown microfibers (BMF), and (b) particulates enmeshed in the fibril matrix comprising sorptive or reactive particulate hydrophobic molecular sieves, the particulates comprising at least 30 and up to 100 weight percent of molecular sieves, the ratio of molecular sieves to matrix being in the range of 40:1 to 1:40, preferably 19:1 to 1:4.

In a further optional step, the sorbed organic component can be isolated by elution or thermal desorption from the extraction medium.

In other further optional steps, the sorbed organic component is irreversibly sorbed and/or subsequently destroyed by catalytic means with the molecular sieve thereby acting as a scavenger for certain analytes.

The articles of the invention are prepared by methods known in the art, including those disclosed in U.S. Pat. Nos. 4,153,661, 5,071,610, and 5,328,758.

What the background art has not taught is the preparation and use of a composite article as a membrane or Sheet material with very favorable diffusion kinetics for sorptive and reactive interactions, the article comprising a porous polytetrafluoroethylene (PTFE) fibril matrix or a nonwoven, preferably melt blown microfiber (BMF), matrix having enmeshed therein hydrophobic siliceous molecular sieves, the composite being useful in solid phase extraction (SPE).

In this application,

"molecular sieve (MS)", which includes zeolite, means inorganic, crystalline materials, usually aluminosilicate compositions, in which the crystal framework of aluminum and silicon atoms forms a three-dimensional network of internal cavities having a honeycomb-like structure.

"zeolite" means a crystalline aluminosilicate with a framework based on an extensive three-dimensional network of oxygen ions. Situated within the tetrahedral sites formed by the oxygen can be either a $Si^{+4}$ or an $Al^{+3}$ ion. The $AlO_2$ tetrahedra in the structure determine the framework charge. This is balanced by cations that occupy nonframework positions (see "Molecular Sieves Principles of Synthesis and Identification" by R. Szostak, Van Nostrand Reinhold, N.Y., pp 1–4);

"membrane", "matrix", and "web" are used interchangeably and mean an open structured entangled mass of fibers;

"silicalite hydrophobic molecular sieves" means a polymorph of $SiO_2$ (mean refractive index 1.39, density 1.76 g/cm.$^3$) having a novel topologic type of tetrahedral framework which contains a large fraction of 5-membered rings of silicon-oxygen tetrahedra, and encloses a 3-dimensional system of intersecting channels, defined by 10-rings of oxygen ions in all three directions. Void spaces occupy about 33% of the crystal volume, and the three-dimensional channel is wide enough to absorb molecules up to about 0.6 nanometers (6 Angstroms) in diameter. The molecular sieves include functionalized and carbon-modified species;

"normal phase system" means a more polar stationary phase with a less polar moving phase;

"reverse phase system" means a less polar stationary phase with a more polar moving phase; and "flexible" means can be wrapped around a pencil without cracking.

The present invention discloses hydrophobic molecular sieve material which can display unique reversed, normal phase, and ion exchange behavior in addition to molecular sieve properties. The mechanisms are not well understood but these separation modes are greatly enhanced when small (at most 10 micrometers, preferably about 3–5 micrometer) diameter particulate is entrapped in an MS particle loaded polytetrafluoroethylene (Empore™ membrane, 3M Company, St. Paul, Minn.) or MS particle loaded BMF membrane disclosed in U.S. Pat. No. 5,328,758. This size particle is conventionally used only in high pressure liquid chromatography because of the pressure drop associated with columns packed with small particles. In other embodiments, molecular sieve particles having an average size of 1 and up to 300 micrometers or more, can be useful. It is particularly surprising that the inorganic MS material appears to be more "hydrophobic" than $C_{18}$ bonded silica. It is also surprising that the MS composite has the demonstrated ability to adsorb molecules which are too large to penetrate the 0.6 nm (6 Angstrom) pores wherein most of the surface area of the particle is exposed. This invention teaches incorporation of these particulate in a highly efficient membrane format yielding composites which have great utility in solid phase extractions/reactions and planar chromatography applications. The membranes show particular selectivity in sorbing certain classes of organic molecules, such as large hydrophobic molecules (e.g., larger than hexane), and small polar molecules (e.g., 2–4 carbon atoms, such as ethanol, propanol, butanol, methyl ethyl ketone, and ethyl acetate) out of water. Multiple analytes can be removed simultaneously.

DETAILED DESCRIPTION OF PREFERRED EMBODIMENTS OF THE INVENTION

It has been found that MS particle-loaded flexible membrane composites preferably having essentially homogeneous compositions and essentially uniform porosity in solid phase extractions (SPE) and reactions provide significant advantages compared to approaches using liquid/liquid extraction (LLE) and other SPE techniques using particle packed columns or cartridges. These particle loaded membrane composites provide a short "flow through" path length. Advantageously, they provide low pressure drop articles in the form of filtration media. This permits use of efficient small particles (10 micrometer or less diameter) with high surface area and controlled interstitial porosity resulting in favorable diffusion kinetics for sorptive interactions. Uniform particle loading and diffusion kinetics of the membrane allow samples to be processed 5 to 10 times faster with less than one tenth the amount of elution solvent conventionally used in LLE. In many applications the composite membranes of the present invention have been found to be superior to composite sheet material or membrane that are loaded with hydrophobic particles such as octadecyl covalently bonded silica ($C_{18}$) which has found great utility as a SPE medium to extract pollutants from air and water. These membranes are now marketed under the "Empore" brand trademark (3M, St. Paul, Minn.).

We have found that inorganic hydrophobic zeolite or molecular sieve material, for example, those commercially available from UOP, Tarrytown, N.Y., is effective in the particle loaded PTFE or BMF format for applications in separation science. Hydrophobic molecular sieve materials have previously been described by Union Carbide and others. The UOP material is marketed under the tradename Abscents™ and preferred materials for use in the present invention comprise 3 to 5 micrometer molecular sieve particles. We prepared membranes from these particles and have tested them for applications in planar chromatography and solid phase extraction. We also have used 250 micrometer particles and prepared polypropylene blown microfiber (BMF) composites. In preferred embodiments, the BMF composites were prepared with polymeric fibers less than 10 micrometers in diameter with higher particle loading capacity than previously described. They can have great utility for large scale remedial applications. These materials function primarily as molecular sieves with internal pores of approximately 0.6 nm (6 Angstroms). This is ideal for the entrapment of small molecules.

This invention teaches flexible composite articles comprising hydrophobic molecular sieve particles in fibrillated polytetrafluoroethylene (PTFE) or BMF matrices with efficient sorption kinetics derived from control of interstitial porosity to form membranes useful in the separation sciences. We were surprised to find that these flexible membranes comprising molecular sieve particles act as efficient hydrophobic solid phase extraction media and display behavior superior to column- or cartridge-type SPE because of faster flow through rates and lower pressure drop. We also found the composite membranes of PTFE and hydrophobic MS particulate to be useful in TLC (thin layer chromatography) and other planar chromatography applications.

The BMF construction has been tested for both air and fluids including water and organics for SPE applications. Gas chromatographic columns have been evaluated with the 250 micrometer particulate and they have been found to be useful.

Molecular sieves and zeolites, or mixtures thereof, useful in this invention are substantially insoluble in aqueous liquid and organic liquid such as water and ethyl acetate, respectively. Specifically, silicalite is a crystalline molecular sieve which cannot be penetrated by water molecule clusters. This invention teaches composite particle loaded membranes or sheet material for the kinetically efficient removal of analytes, preferably organics, from water.

The siliceous molecular sieves suitably employed in the practice of the invention include the microporous crystalline aluminosilicates, i.e. the zeolitic molecular sieves as well as the so-called silica polymorphs. With respect to the latter compositions, their crystal lattices are ideally formed entirely of $SiO_2$ tetrahedral units, but the as-synthesized forms commonly contain at least trace amounts of aluminum derived from aluminum impurities in the synthesis reagents. The aluminosilicate molecular sieves comprise the large class of well-known crystalline zeolites. These high-silica molecular sieves are either commercially available or are prepared by methods, well-known in the art, involving direct hydro-thermal synthesis or involving certain types of crystal lattice dealuminations. A comprehensive review article by E. M. Flanigen concerning both "high" Si/Al zeolites and silica molecular sieves is published in "Proc. 5th Int. Conf. Zeolites, Naples, 1980", L. V. C. Rees, ed., Heyden, London, pp. 760–780. This article is incorporated herein by reference. See also U.S. Pat. No. 4,826,497, particularly cols. 4–6, which is incorporated herein by reference.

In the case of aluminosilicate molecular sieves, those most often used in the practice of the invention have a framework $SiO_2/Al_2O_3$ molar ratio of from at least about 18, preferably at least about 35 to infinity, and more preferably from 200 to 500. All of the siliceous molecular sieves suitably employed have pore diameters of at least 0.55 nm (5.5 Angstroms), preferably at more 0.62 nm (6.2 Angstroms). Preferably the adsorption capacity for water vapor is less than 6 weight percent at Standard Conditions.

The crystalline siliceous molecular sieve may be any suitable form. Typically, the molecular sieve is in powder form or may be aggregated into larger particles, e.g., about 0.5 to 500 or more micrometers in major dimension. The aggregates may be any convenient shape, e.g., spheres, cylinders, free form, or the like. Binders such as silica or alumina may be used when forming aggregates.

Any of the molecular sieves or zeolites may have a spherical shape or irregular shape so long as desirable particulate surface area, specificity, capacity factor (k'), and kinetic diffusion efficiency are present.

In addition to molecular sieves, the flexible SPE webs of the invention may optionally contain additional particles. Suitable optional particles for the purposes of this invention include any particle which can be uncoated or coated with aqueous- or organic-insoluble, sorbent or reactive material or the surface (external and/or internal) of which can be derivatized to provide a coating of insoluble, non-swellable sorbent material. Optional particles include inorganic oxide particles such as silica, alumina, titania, zirconia, and other ceramics to which may be covalently bonded organic groups. Preferred inorganic oxide particulate materials are silica and zirconia because they are commercially available, with silica being particularly preferred because of the ease in bonding a variety of hydrophobic and hydrophilic ligands and coatings onto its surface. Optional particles can be useful as fillers, diluents, processing aids, or to modify properties of the membrane.

Any particles can be useful as long as they do not contribute impurities and/or interfere with SPE or elution techniques in the process.

The present invention further discloses novel carbon coated hydrophobic molecular sieves, preferably silicalite, and hydrophobic molecular sieves having silyl group covalently bonded thereto. Carbon coated molecular sieves can be prepared by a method analogous to that of U.S. Pat. No. 5,108,597, Example 25. Molecular sieves having silyl groups bonded thereto can also be used in the present invention and are prepared by methods known in the art.

A preferred method for preparing the PTFE composite reactive article of the invention comprises the steps of:

a) admixing lubricant (preferably water) with a blend comprising molecular sieves and polytetrafluoroethylene (PTFE) particles to form a soft dough-like mass, the lubricant being present in an amount to exceed the sorptive capacity of the molecular sieves by at least three weight percent, the mass having a cohesive consistency, and the ratio of molecular sieves to PTFE preferably being in the range of 40:1 to 1:40;

b) intensively mixing the mass at a temperature and for a time sufficient to cause initial fibrillation of said PTFE particles;

c) biaxially calendaring the mass between gaps in calendaring rolls maintained at a temperature and for a time, while closing the gap between the calendaring rolls with each successive calendaring operation, to cause additional fibrillation of said PTFE particles to form a self-supporting tear-resistant sheet having a void volume in the range of 30 to 80 percent and a mean pore size in the range of 0.3 to 5.0 micrometers, wherein the void volume and mean pore size vary directly with and are controlled by the amount of lubricant present during processing.

More particularly, detailed preparation of porous fibrous membranes, for entrapment of molecular sieves of the invention therein, can be found in any of U.S. Pat. Nos. 4,153,661, 4,460,642, and 5,071,610, Example 1.

In other embodiments of the present invention, non-PTFE membranes (webs) can compromise non-woven, polymeric macro- or microfibers preferably selected from the group of polymers consisting of polyamide, polyolefin, polyester, polyurethane, polyvinylhalide, or inorganic materials such as glass fiber, or a combination thereof. (If a combination of polymers is used, a bicomponent fiber may be obtained.) If polyvinylhalide is used, it preferably comprises fluorine of at most 75% (by weight) and more preferably of at most 65% (by weight). Addition of a surfactant to such webs may be desirable to increase the wettability of the component fibers.

1. Macrofibers

The web can comprise thermoplastic, melt-extruded, large-diameter fibers which have been mechanically-calendared, air-laid, or spunbonded. These fibers have average diameters in the general range of 50 μm to 1000 μm.

Such non-woven webs with large-diameter fibers can be prepared by a spunbond process which is well known in the art. (See, e.g., U.S. Pat. Nos. 3,338,992, 3,509,009, and 3,528,129, the fiber preparation processes of which are incorporated herein by reference.) As described therein, a post-fiber spinning web-consolidation step (i.e., calendaring) can be used to produce a self-supporting web. Spunbonded webs are commercially available from, for example, AMOCO, Inc. (Naperville, Ill.).

Non-woven webs made from large-diameter staple fibers can also be formed on carding or air-laid machines (such as a Rando-Webber™, Model 12BS made by Curlator Corp., East Rochester, N.Y.), as is known in the art. See, e.g., U.S. Pat. Nos. 4,437,271, 4,893,439, 5,030,496, and 5,082,720, the processes of which are incorporated herein by reference.

A binder is normally used to produce self-supporting webs prepared by the air-laying and carding processes and is optional where the spunbond process is used. Such binders can take the form of resin systems which are applied after web formation or of binder fibers which are incorporated into the web during the air laying process. They are chosen so as not to interfere with performance of the composite webs. Examples of such resin systems include phenolic resins and polyurethanes. Examples of common binder fibers include adhesive-only type fibers such as Kodel™ 43UD (Eastman Chemical Products, Kingsport, Tenn.) and bicomponent fibers, which are available in either side-by-side form (e.g., Chisso ES Fibers, Chisso Corp., Osaka, Japan) or sheath-core form (e.g., Melty™ Fiber Type 4080, Unitika Ltd., Osaka, Japan). Application of heat and/or radiation to the web "cures" either type of binder system and consolidates the web.

Non-woven webs comprising macrofibers have relatively large voids. Therefore, such webs have low capture efficiency of small-diameter particulate (molecular sieves) which is introduced into the web. Nevertheless, particulate can be incorporated into the non-woven webs by at least four means. First, where relatively large particulate is to be used, it can be added directly to the web, which is then calendared to actually enmesh the particulate in the web (much like the PTFE webs described previously). Second, particulate can be incorporated into the primary binder system (discussed above) which is applied to the non-woven web. Curing of this binder adhesively attaches the particulate to the web. Third, a secondary binder system can be introduced into the web. Once the particulate is added to the web, the secondary binder is cured (independent of the primary system) to adhesively incorporate the particulate into the web. Fourth, where a binder fiber has been introduced into the web during the air laying or carding process, such a fiber can be heated above its softening temperature, adhesively capturing particulate which is introduced into the web. Of these methods involving non-PTFE macrofibers, those using a binder system are generally the most effective in capturing particulate. Adhesive levels which will promote point contact adhesion are preferred.

Once the particulate has been added, the loaded webs are typically further consolidated by, for example, a calendaring process. This further enmeshes the particulate within the web structure.

Webs comprising larger diameter fibers (i.e., fibers which average diameters between 50 μm and 1000 μm) have relatively high flow rates because they have a relatively large mean void size.

2. Microfibers

When the fibrous web comprises non-woven microfibers, those microfibers provide thermoplastic, melt-blown polymeric materials having molecular sieves dispersed therein. Preferred polymeric materials include such polyolefins as polypropylene and polyethylene, preferably further comprising a surfactant, as described in, for example, U.S. Pat. No. 4,933,229, the process of which is incorporated herein by reference. Alternatively, surfactant can be applied to a blown microfibrous (BMF) web subsequent to web formation. Particulate (molecular sieves) can be incorporated into BMF webs using the method described in U.S. Pat. No. 3,971,373, the process of which is incorporated herein by reference.

Microfibrous webs of the present invention have average fiber diameters up to 50 μm, preferably from 2 μm to 25 μm, and most preferably from 3 μm to 10 μm. Because the void sizes in such webs range from 0.1 μm to 10 μm, preferably from 0.5 μm to 5 μm, flow through these webs is not as great as is flow through the macrofibrous webs described above.

Disks of the present invention can be used as one of a stack of disks. It has been found advantageous where combinations of contaminants are to be extracted to use a stack of disks (e.g., 2 to 5 or more) having one or more types of particulate per disk, each having optimum extraction efficiency for individual contaminants. Choice of elution solvents depends on contaminants and extraction particulate.

SPE membrane media comprising essentially uniform, small particles (preferably 10 micrometer diameter or less, more preferably 3 to 5 micrometers) with high surface area and controlled, essentially uniform interstitial porosity when embedded in fibrous PTFE matrices have advantages over particle packed column extraction procedures which must utilize larger particles with typical diameters of 40–50 micrometers and which result in larger interstitial porosity. The composite membranes generally have thicknesses in the range of 0.05 to 10 mm, preferably 0.1 to 0.5 mm. The construction allows for a short "flow through" path length resulting in a low pressure drop. Uniform particle loading wherein "channeling" has been eliminated also enhances extraction efficiency. This results in favorable diffusion kinetics for sorptive and reactive interactions not feasible in conventional particle packed columns. Diffusion between particles, whether in columns or matrices, as is known in the art, is governed by Equation 1, below, where $t_d$ is the molecular diffusion time between particles, d is the distance between particles and D is the diffusion coefficient for various fluids. The diffusion time is therefore dependent on the square of the distance between particles. Doubling the distance between particles quadruples the diffusion time and the inter-particle distance is proportional to the ability to close-pack the particles in a column or membrane format. Small particles in narrow diameter high resolution analytical columns require high pressure pumping systems but result in a high pressure drop that is unsuitable for low pressure SPE column applications. Small particles can be ideal for short path length membrane applications.

$$t_d = d^2/2D \qquad \text{Equation 1.}$$

The smaller the particle, the closer the particles can be packed with lower interstitial porosity and $t_d$ can therefore be minimized for higher extraction efficiency with small particles in a membrane or short path flow-through time format. Diffusion coefficient, D, for gaseous systems is 10 to 100 times larger than for fluids and therefore enmeshed particles can be bigger and more widely separated, i.e., larger interstitial porosities are usable. BMF composites can be used therefore with larger particles (50 to 250 micrometer diameter) to efficiently adsorb analytes. A second factor favoring the membrane format is the residence time ($t_r$) the analyte spends in the extraction medium. This is illustrated in Equation 2 where h is the height of the column or thickness of the membrane, $L_v$ is the linear velocity of the fluid flowing through the column or membrane, A is the cross-sectional area of the membrane or $\pi r^2$, r is the column or disk radius, $V_s$ is the volume of sample being passed through the column or membrane, and $t_s$ is the sample process time.

$$t_r = h/L_v = hAt_s/V_s = h\pi r^2 t_s/V_s \qquad \text{Equation 2.}$$

While both particle packed columns with dimensions of h=1 centimeter, r=0.5 centimeter, and particle loaded membranes with dimensions of h=0.05 centimeter, r=2.35 centimeter have approximately the same mass of sorptive particles, the linear flow velocity $L_v$ is over 15 times lower for the membrane, greatly increasing the residence time for adsorption of the analyte.

Sample processing using the particle loaded membranes of the present invention can be 5 to 10 times faster than conventional particle packed columns; membranes typically can utilize less than one tenth the amount of hazardous elution solvent to recover the extracted analyte compared to particle packed columns. This reduction in solvent usage is environmentally very desirable.

Extraction media of the present invention are particularly useful to isolate organic contaminants from fluids, preferably aqueous liquids. Analytes such as hydrocarbons, fluorocarbons, pesticides, herbicides, phenols, or drugs can be isolated efficiently.

Objects and advantages of this invention are further illustrated by the following examples, but the particular materials and amounts thereof recited in these examples, as well as other conditions and details, should not be construed to unduly limit this invention.

EXAMPLES

Example 1 and Comparative A

This trial evaluated sorptive characteristics in the reversed phase mode of a 90:10 percent by weight silicalite:PTFE composite article prepared using the procedure in U.S. Pat. No. 5,071,610, Example 1. The silicalite particles had an average size in the range of 3-5 micrometers. Thin layer chromatographic (TLC) measurements in the reversed phase mode were made to evaluate the hydrophobic character of the silicalite particle/PTFE composite membrane. Analtech Reversed Phase Dye Mixture III,(catalog #30-03, Analtech, Newark, Del.), which comprises fluorescein, Fast Green FCF, Rhodamine and Naphthol Blue Black was used as the reversed phase test dye mixture, along with Disperse Red Dye I (Aldrich Chemical Co., Milwaukee, Wis.) and guaiazulene (Aldrich Chemical Co.), both of which are known hydrophobic dyes used to characterize composite solid phase extraction membranes (see, for example, *Analytica Chimica Acta*, 236, 157-164 (1990)). These dyes are aromatic compounds containing substituents such as phenolic hydroxyl, primary amine, secondary amine, diazo, ketone, aliphatic alcohol, nitro, alkane, cyclic ether, and sulfonic acid groups.

A strip of the 90:10 silicalite:PTFE composite membrane approximately 25 mm×100 mm was spotted about 5 mm from the bottom with each of the test dyes, then suspended in a thin layer chromatographic chamber with the bottom of the strip immersed about 2 mm into a 80:20 methanol:water solution, a known reversed phase elution solvent. The solvent was allowed to run approximately half way up the test strip, after which the test strip was removed and allowed to air dry.

In a parallel, comparative example, the same dyes were chromatographed on a 25 mm×100 mm sheet of a chromatographic article comprising $C_{18}$-bonded silica in a PTFE membrane, prepared as described in U.S. Pat. No. 4,810,381.

The resulting chromatograms indicated that the silicalite-containing composite material behaved as a hydrophobic substrate, mimicking the comparative $C_{18}$:PTFE composite article. In fact, the Disperse Red Dye I was more strongly sorbed onto the silicalite particle than onto the conventional $C_{18}$ particle. It was quite surprising that an inorganic substrate appeared to be more "hydrophobic" than the organic $C_{18}$ covalently bonded substrate of U.S. Pat. No. 4,810,381. While the background art had taught that organic molecules larger than, for example, hexane, would be excluded from the internal pores of the silicalite, this example showed that, surprisingly, the relatively large Disperse Red Dye I molecule was essentially completely sorbed and retained by the silicalite particles.

Example 2

This experiment evaluated adsorptive characteristics in the normal phase mode of a 90:10 percent by weight silicalite:PTFE composite article prepared using the method described in U.S. Pat. No. 5,071,610, Example 1. TLC measurements in the normal phase mode were made to evaluate the sorptive character of the silicalite particle/PTFE composite membrane using Analtech Test Dye Mixture IV (catalog #30-04, Analtech, Newark, Del.), which comprises Fast Red 7B, Sudan Green-Yellow, Sudan II-Peach, Sudan II-Red, Sudan Blue and Sudan Green-Blue, along with Disperse Red Dye I and guaiazulene. The compounds of Test Dye Mixture IV were generally more hydrophobic than those of Test Dye Mixture III (Example 1), and comprised aromatic compounds containing substituents such as phenolic hydroxyl, secondary amine, diazo, ketone, and aliphatic substituents.

A strip of the 90:10 silicalite:PTFE composite membrane approximately 25 mm×100 mm was spotted about 5 mm from the bottom with each of the test dyes, then suspended in a thin layer chromatographic chamber with the bottom of the strip immersed about 2 mm into a toluene reservoir. The solvent was allowed to run approximately half way up the test strip, after which the test strip was removed and allowed to air dry.

The resultant chromatogram was quite comparable to the comparative example using $C_{18}$-bonded silica particles in a PTFE membrane (Example 1). Thus, the silicalite TLC sample appeared to act as a normal phase substrate. This example showed that molecular sieves act as sorptive substrates for molecules larger than 0.6 nm in size as well as "inclusion" or "trapping" substrates for molecules smaller than 0.6 nm.

Example 3

A blown microfiber sheet-like article comprising silicalite molecular sieves was prepared essentially as described in U.S. Pat. No. 5,328,758, Example 1. Silicalite particles of approximately 200 micrometer mean diameter (Abscents™ molecular sieves, UOP, Tarrytown, N.Y.) were enmeshed in a web of Exxon type 3495G™ polypropylene (Exxon Corp., Baytown, Tex.). The particle-loaded microfiber article had a weight of 120 g/m², for a loading percentage of 66% by weight, and a thickness of approximately 0.35 mm. The article had an air permeability value (Gurley time) of 0.5 seconds/50 cc. Air permeability was measured using a model 4110 NY 5826 Gurley densometer (W. & L. E. Gurley Co., Troy, N.Y.). This article can be used as a chromatographic or solid phase extraction article.

Example 4 and Comparative B

A one liter sample of reagent grade water was spiked with a 5 ml aliquot of methanol containing Disperse Red 1 to give a solution mimicking a hydrophobic pollutant at the 100 ppb level. A 47 mm disk was cut from the MS composite prepared as described in Example 1 and placed in a Millipore™ filtration apparatus (Millipore Corp., Bedford, Mass.). The disk was pre-wetted with methanol for comparative purposes. The water sample was then pulled through the PTFE disk using a vacuum source and the Disperse Red 1 dye was adsorbed on the disk. The dye was then eluted from the disk with 2–10 ml aliquots of methanol and brought to volume in a 25.0 mL volumetric flask. The dye concentration in the eluant was then measured spectrophotometrically at 480 nanometers. This experiment was repeated but 0.1N KOH in methanol was used as the elution solvent. Calibration solutions of the dye in both methanol and 0.1N KOH/methanol were used to quantitate the recovery of the dye eluted from the two disks. Dye recovery for the methanol only eluant was 68.9% while the recovery for the KOH/methanol was 97.5%. The time required to process the liter samples was less than 20 minutes. These results were in accordance with the TLC elution profiles described in earlier examples.

Comparative B: Two one liter samples of reagent grade water were spiked with a 5.0 mL aliquot of methanol containing Aldrich Disperse Red #1 dye to give a solution similar to that of this Example 4. Polypropylene tubes (1 cm×6 cm) were packed with deactivated glass wool, approximately 0.5 g of 250 μm silicalite*, and topped with non-particle loaded non-woven webs held in place with plastic rings. The tubes were dry packed, but the beds were compressed further upon addition of conditioning solvent. The tubes were conditioned with 2×10 mL aliquots of methanol and rinsed with a 10 mL portion of water. The liter samples were then processed under negative pressure using a water aspirator. The samples were then eluted with a 2×10 mL methanol rinse, or a 2×10 mL methanol/0.1M KOH rinse, respectively. The eluants were brought to volume in 25.0 mL volumetric flasks, and analyzed spectrophotometrically at 480 nm. For quantitation, standards were also prepared and analyzed at 480 nm. Both neutral and basic standards were prepared to account for any matrix differences. Dye recovery for the methanol only eluant was 32.8%, while the KOH/methanol recovery was 70.8%. Additionally, the time required to process 1L of water under these conditions was well over an hour.

Data of Example 4 and Comparative B show that for comparable quantities of particulates in a cartridge and in a disk format, the disk provided superior recoveries of analyte in a much shorter period of time.

*commercially available as Abscents-5000; silicalite particles of 3–5 micrometer diameter could not be used because water would not flow through the tube, even using vacuum.

Example 5 and Comparative C

This Example illustrates the adsorption and desorption behavior of the MS particulate for aliphatic hydrocarbon and fluorocarbon test probe molecules. In this case, a gas chromatographic column was prepared using 250 micrometer diameter Abscents™-5000 (UOP, Des Plaines, Ill.) particulate. The column was one meter long, 2.8 mm outside diameter stainless steel tubing and the particulate was contained using quartz glass wool plugs at the inlet and outlet ends of the column. The column was installed in a Hewlett Packard Model 5890 gas chromatograph and conditioned at 250° C. for 18 hours to remove any entrapped volatile organic compounds with a helium carrier gas flow of 1 milliliter per minute. A flame ionization detector was used to detect components eluted from the column in subsequent tests. Samples of methane, ethane, propane, butane, pentane, hexane, heptane, octane, and their perfluorinated analogs were then injected individually into the inlet end of the column and their retention times upon exiting the column were measured to establish the gas solid partitioning characteristics of the particulate. The particle packed column was at an initial temperature of 60° C. for 2 minutes and then linearally programmed to 250° at 10° per minute. Fluorocarbon probes were selected to test the molecular size separation characteristics of the particulate because of their known sorptive inertness. Data in Table 1, below, shows the retention times observed. It was surprising to find that the smaller fluorocarbon molecules, perfluoromethane, perfluoroethane, and perfluoropropane were more strongly adsorbed and were eluted after the hydrocarbon analogs, methane, ethane, and propane. Perfluorobutane, perfluoropentane, and perfluorohexane, however, eluted before butane, pentane, and hexane. Perfluoroheptane, perfluorooctane, heptane, and octane analogs then appeared to have the same elution characteristics. This is shown in Table 1, below.

TABLE 1

GC retention time vs carbon number of test probes on Abscents-5000

| Carbon Number | Compound (Retention Time in Minutes) | | | |
|---|---|---|---|---|
| 1 | CH$_4$ | (0.95) | CF$_4$ | (1.86) |
| 2 | C$_2$H$_6$ | (5.99) | C$_2$F$_6$ | (7.56) |
| 3 | C$_3$H$_8$ | (11.48) | C$_3$F$_8$ | (12.57) |
| 4 | C$_4$H$_{10}$ | (16.55) | C$_4$F$_{10}$ | (15.55) |
| 5 | C$_5$H$_{12}$ | (20.60) | C$_5$F$_{12}$ | (19.72) |
| 6 | C$_6$H$_{14}$ | (24.21) | C$_6$F$_{14}$ | (23.61) |
| 7 | C$_7$H$_{16}$ | (27.36) | C$_7$F$_{16}$ | (27.00) |
| 8 | C$_8$H$_{18}$ | (32.83) | C$_8$F$_{18}$ | (33.00) |

The data of Table 1 show silicalite is useful in the chromatographic separation of small and intermediate size hydrocarbon and fluorocarbon molecules.

Example 6 and Comparative D

This Example illustrates the chromatographic behavior of carbon coated silicalite in a GC column using the same conditions as in Example 5. Abscents™-5000 particulate in this case was placed in a reaction chamber which was then evacuated. Butyl alcohol was admitted to the chamber and the temperature was raised to 700° C. as described in U.S. Pat. No. 5,108,597. After 45 minutes the chamber was cooled to room temperature and the black carbon coated particulate was removed and sealed in a capped vial. This composite material was then packed in a GC column and evaluated for its adsorption/desorption properties for a comparison with the uncoated particulate described in Example 5. The data of Table 2, below, shows the retention times observed.

TABLE 2

GC retention time vs carbon number of test probes on carbon modified Abscents-5000

| Carbon Number | Compound (Retention Time in Minutes) | | | |
|---|---|---|---|---|
| 1 | $CH_4$ | (1.41) | $CF_4$ | (2.71) |
| 2 | $C_2H_6$ | (7.27) | $C_2F_6$ | (8.90) |
| 3 | $C_3H_8$ | (13.04) | $C_3F_8$ | (14.18) |
| 4 | $C_4H_{10}$ | (18.31) | $C_4F_{10}$ | (17.68) |

The data of Table 2 show that the carbon coated material yielded longer retention times for the probe molecules tested which indicated stronger adsorption behavior than the uncoated material. Butyl alcohol was able to penetrate into the 0.6 nanometer (6 Angstrom) pores and was converted to molecular carbon therein. This was a new form of carbon-coated particulate which displayed sorptive properties different from those expected for materials with larger pores. The same retention time inversion occurred between the fluorocarbon and hydrocarbon molecules having 4 carbon atoms as was found with the uncoated particulate.

The MS particulate of this example can be enmeshed in a PTFE or melt-blown web and used as a chromatographic or solid phase extraction article.

Example 7 and Comparative E

This Example illustrates the modification of silicalite by formation of covalently bonded silyl groups with available reactive sites on the particulate. One hundred grams of Abscents-5000 particulate were added to a 500 ml three-necked flask fitted with a mechanical stirrer, reflux condenser, nitrogen bubbler, and oil bath heating apparatus. One hundred fifty grams of hexamethyldisilazane were added and an exotherm was noted. Slow nitrogen bubbling was started and the flask was heated to 130° C. to obtain reflux conditions. This reaction was maintained for 24 hours and after cooling, the silazane was decanted off. The particulate was transferred to a glass crystallizing dish and placed in an aspirator vacuum oven at 150° C. for 1 hour. A slight odor of ammonia was detected at this point. The aspirator vacuum was then connected with a high vacuum source and the pressure was reduced to 0.075–0.2 mm Hg. This condition was maintained for 23 hours before the vacuum was released and the resulting particulate was transferred to an oven dried glass jar. No ammonia odor was detected. The weight of the recovered particulate was 102.12 grams, indicating that about 2 percent by weight methyl silyl groups had been added to the silicalite. This silylation reaction is known in the art to render hydrophilic surfaces more hydrophobic. The chromatographic behavior of silyl-modified silicalite was then evaluated in a GC column using the same conditions as in Example 5. Table 3 shows the data obtained for the test probe molecules used in Example 6 following the procedure of Example 5.

TABLE 3

GC retention time vs carbon number of test probes on silane modified Abscents-5000

| Carbon Number | Compound (Retention Time in Minutes) | | | |
|---|---|---|---|---|
| 1 | $CH_4$ | (1.22) | $CF_4$ | (2.41) |
| 2 | $C_2H_6$ | (6.67) | $C_2F_6$ | (8.32) |
| 3 | $C_3H_8$ | (12.18) | $C_3F_8$ | (13.26) |
| 4 | $C_4H_{10}$ | (17.19) | $C_4F_{10}$ | (15.80) |

These data indicate that silyl derivatized particulate has a stronger sorptive interaction with hydrophobic test probe molecules than the untreated silicalite. The same retention time inversion occurred between the fluorocarbon and hydrocarbon molecules having 4 carbon atoms as found with the uncoated and the carbon coated particulate.

The MS particulate of this example can be enmeshed in a PTFE or melt-blown web and used as a chromatographic or solid phase extraction article.

Example 8

This example describes a process for removing volatile fluorochemicals from a gaseous hydrogen matrix, for example, as found with electrochemical fluorination (ECF) cells. A 7.6 μm (three inch) long stainless steel tube 0.66 cm (¼ inch) outer diameter was packed with 250 micrometer diameter silicalite particulate held in place with a quartz glass wool plug at the inlet and outlet. A typical ECF gas sample was then allowed to flow through the tube at ambient temperature and the resulting exit gas analyzed by gas chromatography using an atomic emission detector (AED) Hewlett Packard. This detector was set to detect only fluorine at 690 Angstroms wavelength. A sample of the original cell gas was also analyzed for comparison. Chromatograms of the fluorocarbon components present before and after passage through the particulate showed separation of the components. Peaks were perfluoromethane, perfluoroethane, sulfurhexafluoride, perfluoropropane, perfluorobutane, and perfluoropentane respectively. Full scale sensitivity response before silicalite treatment was 1100 while the chromatogram full scale sensitivity after silicalite treatment was 4. This indicates that over 99.7 percent of the fluorocarbons were removed by the passage through silicalite.

The MS particulate of this example can be enmeshed in a PTFE or melt-blown web and used as a chromatographic or solid phase extraction article.

Example 9

This example describes the separation of hydrocarbon and fluorocarbon olefins using silicalite, carbon derivatized silicalite (Example 6), and silyl derivatized silicalite (Example 7). In this case the same GC conditions were used as described in Example 5 for the separation of hydrocarbon and fluorocarbon alkanes. Table 4 lists retention times vs carbon number of olefinic test probes on carbon modified silicalite, and Table 5 lists the retention times for the olefinic probes on the silyl derivatized silicalite.

TABLE 4

Olefinic separations on carbon coated Silicalite

| Carbon Number | Compound (Retention Time in Minutes) | | | |
|---|---|---|---|---|
| 2 | $C_2H_4$ | (9.85) | $C_2F_4$ | (7.77) |
| 3 | $C_3H_6$ | (16.54) | $C_3F_6$ | (—) |
| 4 | $C_4H_8$ | (NA) | $C_4F_8$ | (16.56) |
| 4* | $C_4H_8$ | (NA) | $C_4F_8$ | (—) |

*Isobutylene and perfluoroisobutylene
NA = not available

It was surprising to find that perfluoroisobutylene and perfluoropropylene did not elute from the GC column containing the uncoated or the carbon coated silicalite.

TABLE 5

Olefinic separations on silane derivatized Silicalite

| Carbon Number | Compound (Retention Time in Minutes) | | | |
|---|---|---|---|---|
| 2 | $C_2H_4$ | (8.41) | $C_2F_4$ | (7.18) |
| 3 | $C_3H_6$ | (14.46) | $C_3F_6$ | (12.33) |
| 4 | $C_4H_8$ | (20.00) | $C_4F_8$ | (15.14) |
| 4* | $C_4H_8$ | (NA) | $C_4F_8$ | (—) |

*Isobutylene and perfluoroisobutylene

While perfluoroisobutylene did not elute from any of silicalite columns, perfluoropropylene did elute from the silyl derivatized silicalite. U.S. Pat. No. 5,300,714 discloses an ambient temperature process for removal of toxic perfluoroisobutylene from inert fluorocarbons using certain inorganic oxides including basic alumina. It was surprising to find this similar reactivity with the silica-based silicalite and its derivatives. In the former case, it was demonstrated that the perfluoroisobutylene was destroyed with the production of fluoride ion. It appears that this is the situation in the present invention since similar high temperatures (250° C.) were necessary to thermally desorb perfluoroisobutylene. Silicalite and derivatives described in this invention provide a process for removing toxic perfluoroisobutylene. It appears also that silyl derivatization deactivates certain reactive sites on silicalite since perfluoropropylene did not elute using untreated and carbon coated silicalite. Data in Table 5 show that the hydrocarbon alkenes are more strongly adsorbed than the fluorocarbon alkenes since higher elution temperatures and times were observed. This is contrary to results obtained for alkanes and perfluoroalkanes having fewer than three carbon atoms as listed in Table 3.

Various modifications and alterations of this invention will become apparent to those skilled in the art without departing from the scope and spirit of this invention, and it should be understood that this invention is not to be unduly limited to the illustrative embodiments set forth herein.

We claim:

1. A method of concentrating by sorption or reaction of at least one organic contaminant from an organic fluid comprising the step of passing an organic fluid containing said at least one organic contaminant through or by at least one solid phase extraction or chromatographic medium comprising
   (a) a matrix comprising fibrillated polytetrafluoroethylene (PTFE) fibrils or blown microfibers (BMF), and
   (b) particulates enmeshed in the fibrous matrix comprising hydrophobic siliceous sorptive or reactive particulate molecular sieves having pore diameters in the range of about 5.5 to 6.2A, the ratio of molecular sieves to matrix being in the range of 40:1 to 1:40,
   said medium having an essentially homogeneous composition and essentially uniform porosity and being useful to remove organics from organic fluids.

2. The method according to claim 1 further comprising the step of eluting or thermally desorbing the resulting adsorbed Organic component.

3. The method according to claim 1 wherein said organic component is a small polar molecule.

4. The method according to claim 1 wherein said nonwoven matrix of said medium is fibrillated polytetrafluoroethylene.

5. The method according to claim 1 wherein said nonwoven matrix of said medium is blown microfibers.

6. The method according to claim 5 wherein said blown microfibers are selected from the group consisting of polyamide, polyolefin, polyester, polyurethane, glass fiber, and polyvinylhalide.

7. The method according to claim 1 wherein said molecular sieves of said medium are selected from the group consisting of aluminosilicate molecular sieves having a Si:Al ratio of at least 18.

8. The method according to claim 1 wherein said molecular sieves of said medium are zeolites.

9. The method according to claim 1 wherein said ratio of molecular sieves to matrix of said medium is 19:1 to 1:4.

10. The method according to claim 1 wherein said medium is useful in chromatographic applications.

11. The method according to claim 1 wherein said medium is useful in solid phase extraction applications.

12. The method according to claim 1 wherein said particulate molecular sieves enmeshed in said matrix are carbon coated hydrophobic siliceous molecular sieves.

13. The method according to claim 1 wherein said particulate molecular sieves enmeshed in said matrix comprise silyl groups covalently bonded thereto.

14. The method according to claim 1 wherein said molecular sieves of said medium have a size in the range of 1 to 300 micrometers.

15. The method according to claim 1 wherein said molecular sieves of said medium have a size in the range of 3 to 5 micrometers.

16. The method according to claim 1 wherein said medium has a thickness in the range of 0.05 to 10 mm.

17. The method according to claim 1 wherein said particulates enmeshed in said matrix comprise (1) at least 30 and up to 100 weight percent of hydrophobic siliceous molecular sieves, and (2) 70 to 0 weight percent of organic-coated or uncoated particulates different from said hydrophobic molecular sieves.

18. The method according to claim 1 wherein said particulate molecular sieves enmeshed in said matrix are silicalite.

19. The method according to claim 1 wherein said medium comprises a stack of at least two disks wherein at least one disk is said solid phase extraction or chromatographic medium.

20. The method according to claim 1 wherein said organic component is a hydrophobic molecule.

21. The method according to claim 1 wherein said organic component is a fluorocarbon molecule.

22. The method according to claim 1 wherein said organic component is a hydrocarbon.

* * * * *